United States Patent [19]

Klemm

[11] Patent Number: Plant 7,374

[45] Date of Patent: Oct. 30, 1990

[54] GERANIUM NAMED KLEFIZON

[75] Inventor: Siegfried Klemm, Stuttgart, Fed. Rep. of Germany

[73] Assignee: Klemm & Sohn, Stuttgart-Muhlhausen, Fed. Rep. of Germany

[21] Appl. No.: 356,126

[22] Filed: May 24, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Charles W. Rummler

[57] ABSTRACT

A new and distinct Geranium cultivar particularly distinguished by its continuous and profuse production of large flower clusters comprising very large semi-double florets of a pink salmon color that does not fade in great heat, the flower clusters having an average diameter of 10 to 12 cm. and containing 40 to 50 florets of a diameter of about 5.5 cm. Each of these flower clusters stands on a strong light brown stalk of 11 to 12 cm. long and well above a light green foliage body of medium sized kidney shaped leaves which grown in a round body having a height of about 28 cm. above the soil, measured below the flower clusters. The floral persistance is very good with a lasting quality of about 17 to 18 days and the whole plant shows resistance against botrytis.

1 Drawing Sheet

BACKGROUND OF THE NEW PLANT

This new Geranium variety was found by me in the Summer of 1979 as a mutation after meristeming "Pink Camelia" at my nursery at Stuttgart, West Germany and it has been grown there under controlled conditions since its discovery and especially during the last four years when it has been noted to be outstanding compared with both old and new varieties and because of that, I have propagated this discovery plant by means of cuttings, for both indoor and outdoor growing, through successive generations whereby it was found that the homogeniety of this plant can be assured. I have found that because of its flori-ferousness and its outstanding color this new plant has a great market value.

DESCRIPTION OF THE DRAWING

My new Geranium cultivar is illustrated by the accompanying full-color photographic drawing which shows a potted plant in bloom and illustrating the general characteristics of this variety with respect to both the foliage, the blossoms, and the bud clusters, the color shown being as true to that herein specified as is reasonably possible to obtain by conventional professional photographic procedures.

DESCRIPTION OF THE NEW PLANT

The following is a detailed description of my new Geranium cultivar based upon observations made in 1988 of plants grown both in greenhouse as well as outdoors and the color designation is according to The R.H.S. Colour Chart published by the Royal Horticultural Society of London, England.

THE PLANT

Origin: Sport.
Parent Variety: Pink Camelia (unpatented).
Classification:
- *Botanic.*—*Pelargonium zonale* hybrid.
- *Commercial.*—Potted Geranium.

Form: An attractive bush.

Height: About 28 to 30 cm. in September below the flower clusters.
Growth: Strong and spreading.
Branching character: Good.
Foliage:
- *Quantity.*—Normal for Pelargonium.
- *Leaf size.*—About 6 to 9 cm. wide.
- *Leaf shape.*—Generally reniform with bicrenate margin.
- *Texture.*—Smooth.
- *Color.*—Upper side — Medium green with very little zonation. Under side — Light green.

Ribs and veins: About 5 to 7 veins for each leaf.

THE BUD

Size: Normal.
- *Diameter.*—About 6 to 7 mm. just before opening.
- *Length.*—About 13 mm.

Shape: Ovoid with acuminate apex.
Rate of opening: Rapid.
Color of florets:
- *When sepals first divide.*—Orange salmon.
- *When petal begin to unfurl.*—Pink salmon.

Sepals:
- *Number.*—Five.
- *Shape.*—Linear.
- *Character.*—The sepals stand up when the flower is open.
- *Color.*—Inside — Light green. Outside — Green with brown shading.

Calyx:
- *Size.*—Broad.
- *Shape.*—Cup-shaped.
- *Splitting.*—The calyx does not split.
- *Aspect.*—Very little hairs.

Flower stem:
- *Length.*—About 13 to 17 cm.
- *Character.*—Strong and erect.
- *Color.*—Light brown.

THE INFLORESCENCE

Blooming habit: Continuous and profusely from early Spring through late Midseason.

Size of flower cluster: Very large, about 10 to 12 cm. in diameter.

Florets:

*Size.*—Very large. Diameter — About 5.2 to 5.5 cm. Depth — About 1.5 cm.

Borne: Singly on an umbel stem, there being from 40 to 50 florets in each umbel formed cluster.

Petalage:

*Number of petals.*—Five to seven.

*Arrangement.*—Imbricated.

*Form.*—Reniform with entire margin.

*Texture.*—Soft.

*Appearance.*—Satiny.

*Color.*—Petal body, Pink salmon — RHS 43-B. Base — RHS 43-C. Reverse side — RHS 43-D.

Phyllaries:

*Number.*—One to three.

Flower stem:

*Length.*—About 11 to 17 cm.

*Character.*—Strong and upright.

*Color.*—Light brown.

Persistence: When the florets are old, the petals dry and fall off leaving a clean flower cluster.

Disease resistance: Resistant to botrytis as observed at Stuttgart from 1985 through 1988.

Lasting quality of florets: About seventeen to eighteen days.

THE REPRODUCTIVE ORGANS

Stamens:

*Number.*—Seven.

*Arrangement.*—Encircling the pistil.

*Anthers.*—Size: About 1 to 2 mm. Color: Salmon.

*Filaments.*—Length: About 4 mm.Color: Frosted glass.

*Pollen.*—Color: Orange.

Pistils:

*Number.*—One with five arms.

*Style.*—Length: About 6 mm. Color: Half green, half salmon.

*Stigmas.*—Color: Frosted salmon.

Character of ovaries: Typical for pelargonium.

THE FRUIT

Fertility: The fruit is fertile.

Shape: Ovoid.

Color at maturity: Dark brown.

I claim:

1. The new and distinctive Geranium plant, substantially as herein shown and described, particularly distinguished by its clear pink salmon coloration and the relatively large size of its flower clusters and the large size and number of florets comprised in each cluster.

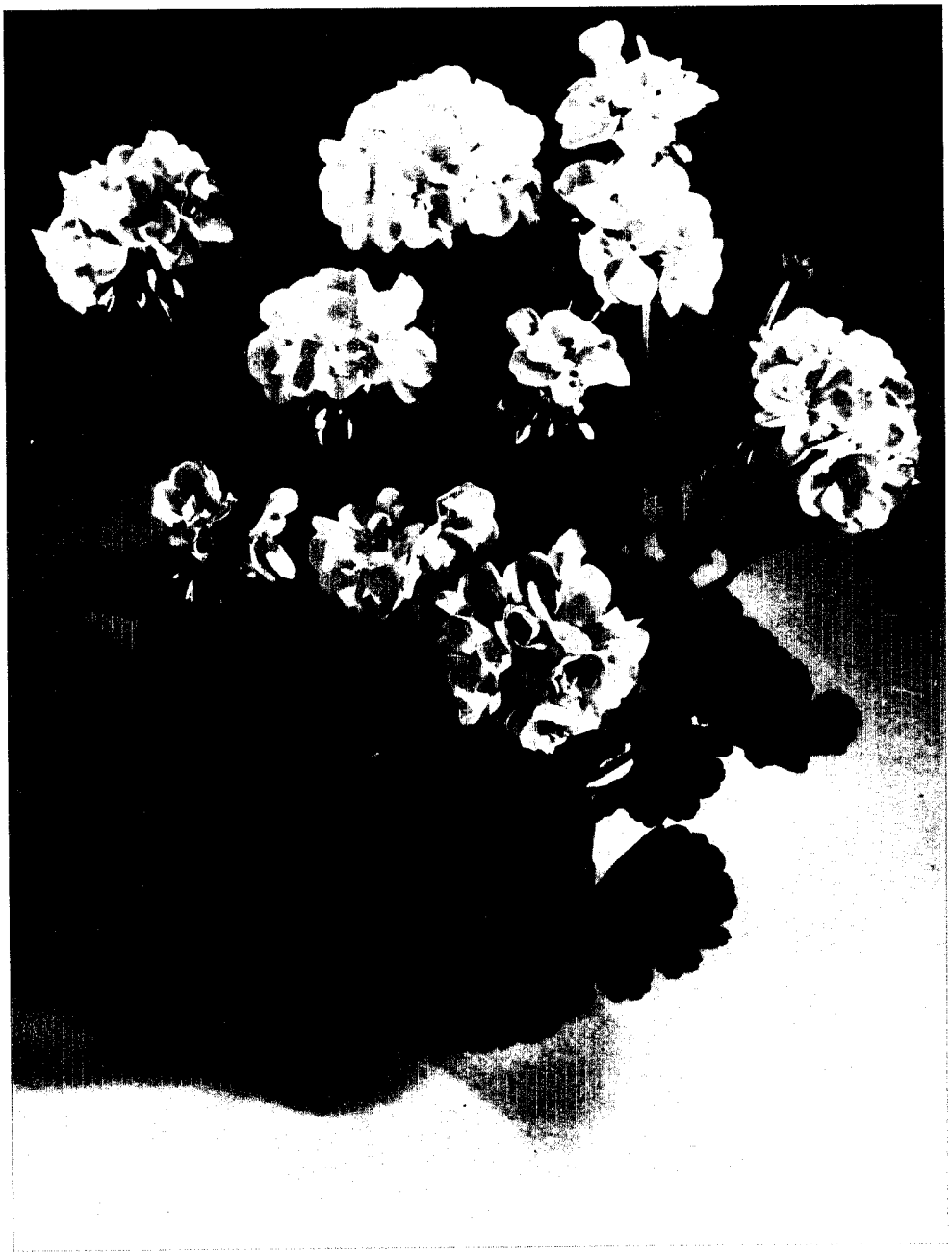

* * * * *